United States Patent [19]

Okada

[11] 4,248,789

[45] Feb. 3, 1981

[54] PROCESS FOR PRODUCING CATECHINS

[75] Inventor: Fumio Okada, Makurazaki, Japan

[73] Assignee: Director of National Research Institute of Tea, Shizuoka, Japan

[21] Appl. No.: 103,038

[22] Filed: Dec. 13, 1979

[30] Foreign Application Priority Data

Feb. 7, 1979 [JP] Japan .................................. 54/12212

[51] Int. Cl.$^3$ ........................................... C07D 311/62
[52] U.S. Cl. ................................................. 260/345.2
[58] Field of Search ...................................... 260/345.2

[56] References Cited

U.S. PATENT DOCUMENTS 4,166,861   9/1979   Bonati et al. ..................... 260/345.2

*Primary Examiner*—Nicky Chan
*Attorney, Agent, or Firm*—Frishauf, Holtz, Goodman & Woodward

[57] ABSTRACT

A process for producing catechins from tannic substance which has been extracted from tea leaves. An aqueous solution of the extract is admixed with an aqueous solution of caffeine to form a liquid-containing mixture of free catechins and a precipitated mixture of ester-type catechins. The caffeine is then removed from the aforesaid mixtures, and the respective mixtures fractionated to obtain epicatechin, epigallocatechin, epicatechin gallate, and epigallocatechin gallate.

9 Claims, 6 Drawing Figures

PROCESS FOR PRODUCING CATECHINS

BACKGROUND OF THE INVENTION

This invention relates to a process for the production of catechins, more particularly to a process for producing catechins using tea leaves as a raw material.

Various studies concerning tea have been made for a long time. This invention is directed to the development of a new use of tea leaves and to a process for the production of catechins, in which four types of catechins (epicatechin, epigallocatechin, epicatechin gallate and epigallocatechin gallate) can be isolated simultaneously from polyphenol substances contained in tea leaves in large quantities and if desired, each of the components can be obtained in the form of crystals.

The pharmaceutical effects of tea have been elucidated in considerable detail, whereas the characteristics and utility of tea catechin components have not been fully studied because of difficulties in their isolation and crystallization, although they have drawn attention in many fields.

In the continual study of the components of tea since 1965, we discovered that tea tannin inhibits infection from plant virus. We continued work on a process for obtaining each of four catechins in the form of crystals in a large quantity, in order to clarify the effects of the components of tea tannin, i.e. tea catechins.

THE INVENTION

We discovered that each of the catechin components of tea have the property of forming a mixed crystal with caffeine having a purine base. When an aqueous solution of caffeine is added to an aqueous solution of a catechin mixture extracted and separated from tea leaves, caffeine bonds to the ester-type catechins to form a precipitate, and a liquid upper phase. It was found that this phenomenon occurs most completely at low temperatures (0°–10° C., preferably about 3°–7° C.), so that the upper phase (liquid layer) separates clearly from the lower phase (precipitate layer). The upper phase primarily contains the free catechins (epicatechin, epigallocatechin) and the lower phase contains the ester-type catechins (epicatechin gallate, epigallocatechin gallate).

This invention provides a process for producing catechins, which comprises adding an aqueous solution of caffeine to an aqueous solution of tannic substance extracted from tea leaves to obtain free catechins and ester-type catechins.

This invention also provides a process for producing catechins, characterized by adding an aqueous solution of caffeine to an aqueous solution of tannic substance to separate into a group of the free catechins and a group of the ester-type catechins, removing caffeine, and then fractionating each component of epicatechin, epigallocatechin, epicatechin gallate and epigallocatechin gallate with a distribution solvent on a column of Sephadex, and thereafter, if desired, crystallizing each component.

DETAILED DESCRIPTION OF THE INVENTION

Figure 1:
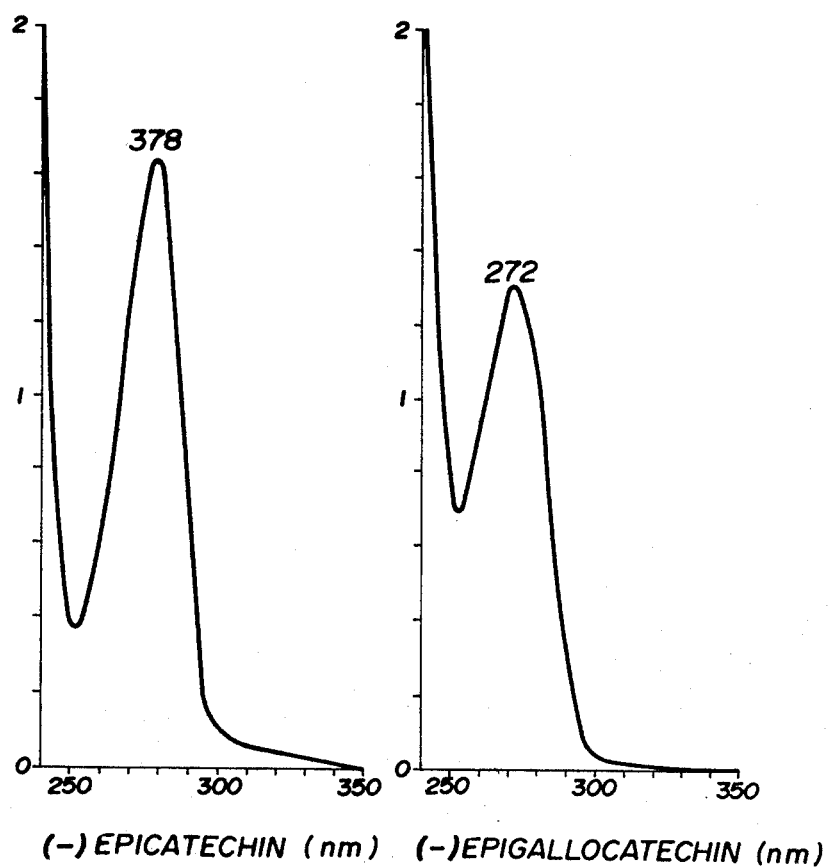
FIG. 1 is the ultraviolet absorption spectrum of the free catechins.
Figure 2:
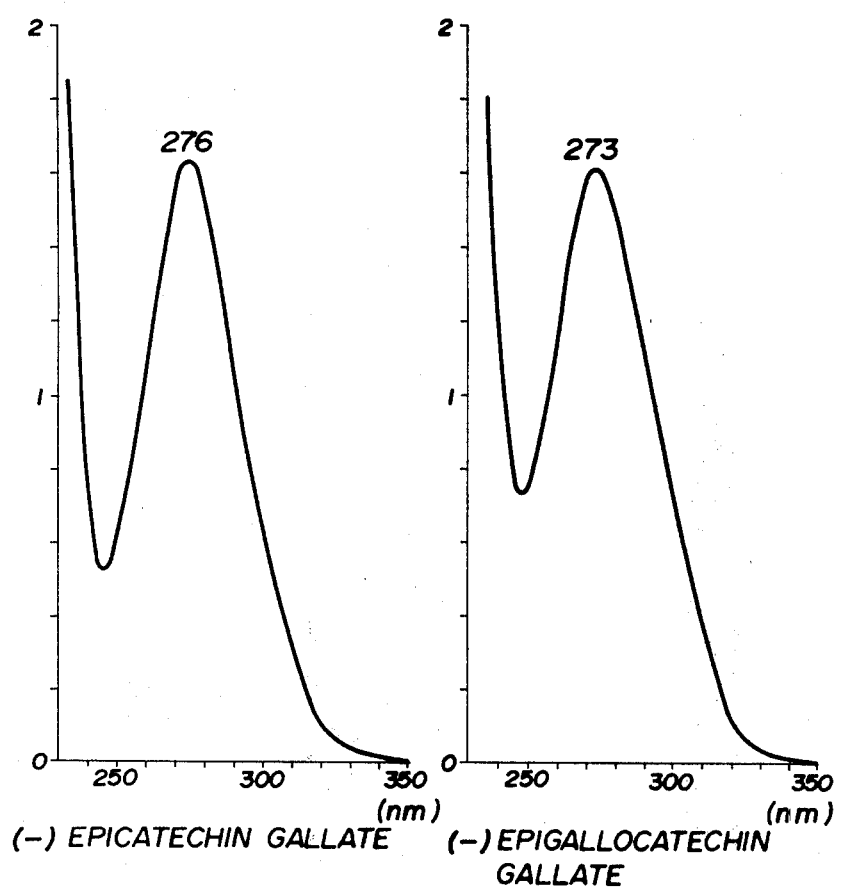
FIG. 2 is the ultraviolet absorption spectrum of the ester-type catechins.
Figure 3:
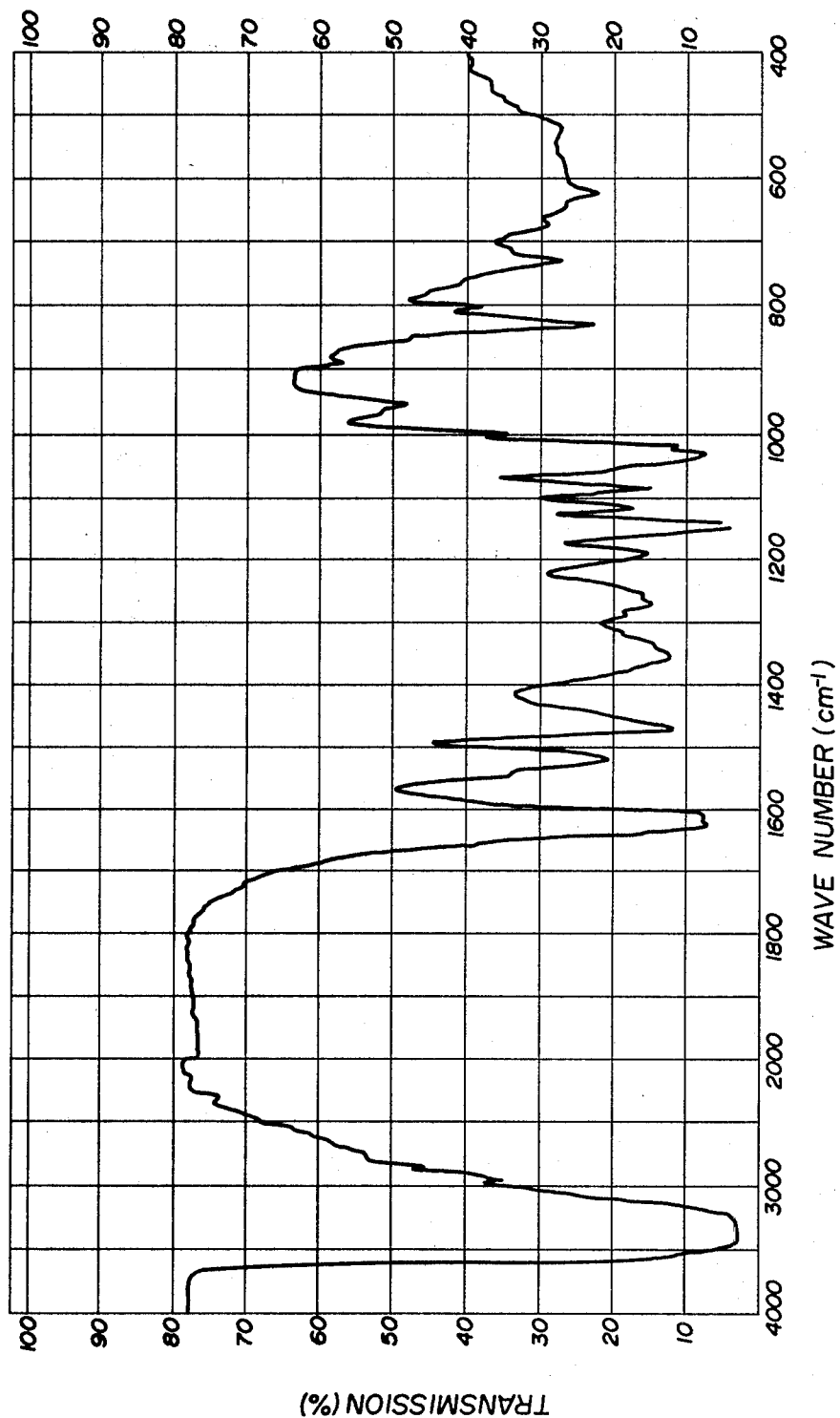
FIG. 3 is the infrared absorption spectrum of (—)epicatechin.
Figure 4:
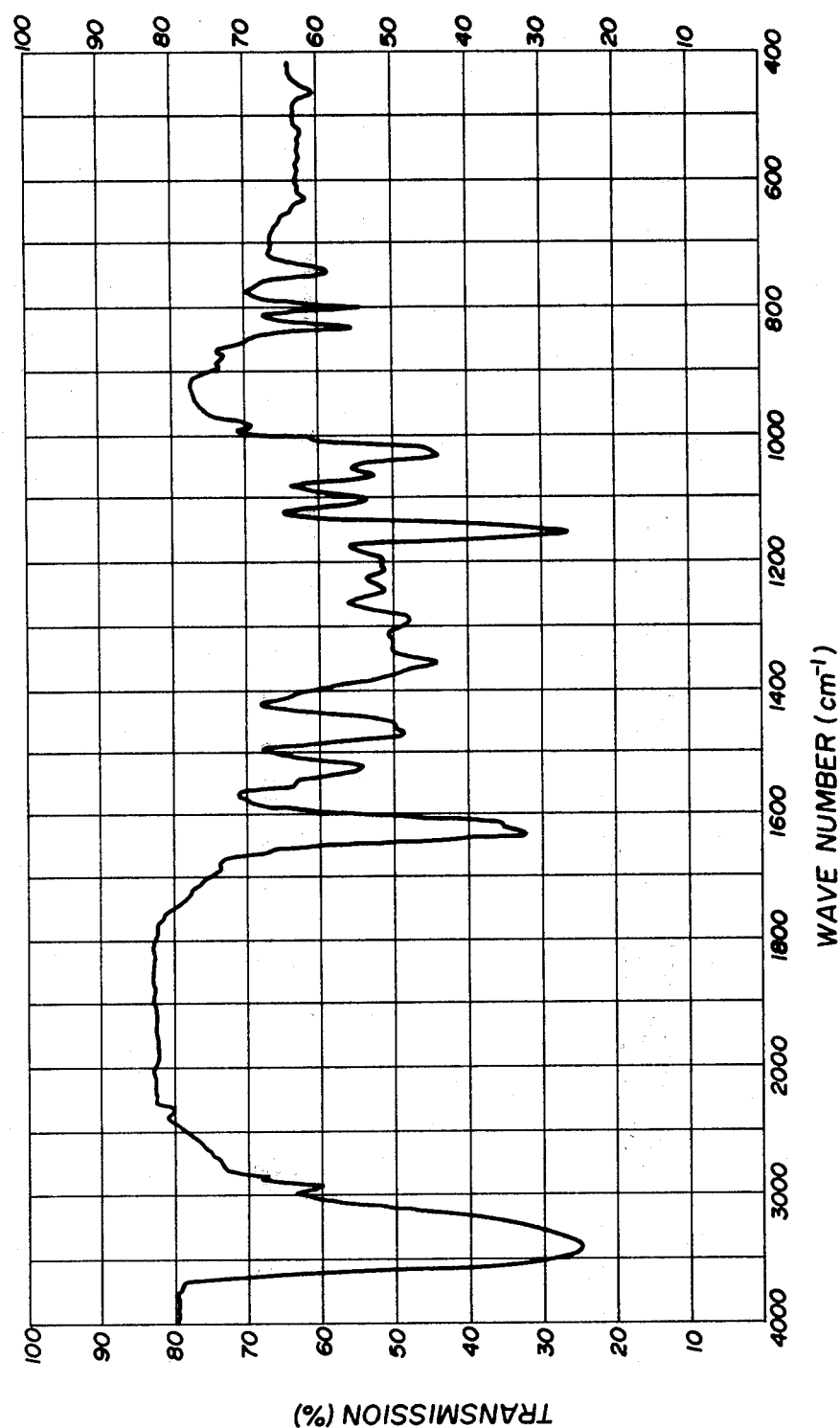
FIG. 4 is the infrared absorption spectrum of (—)epigallocatechin.
Figure 5:
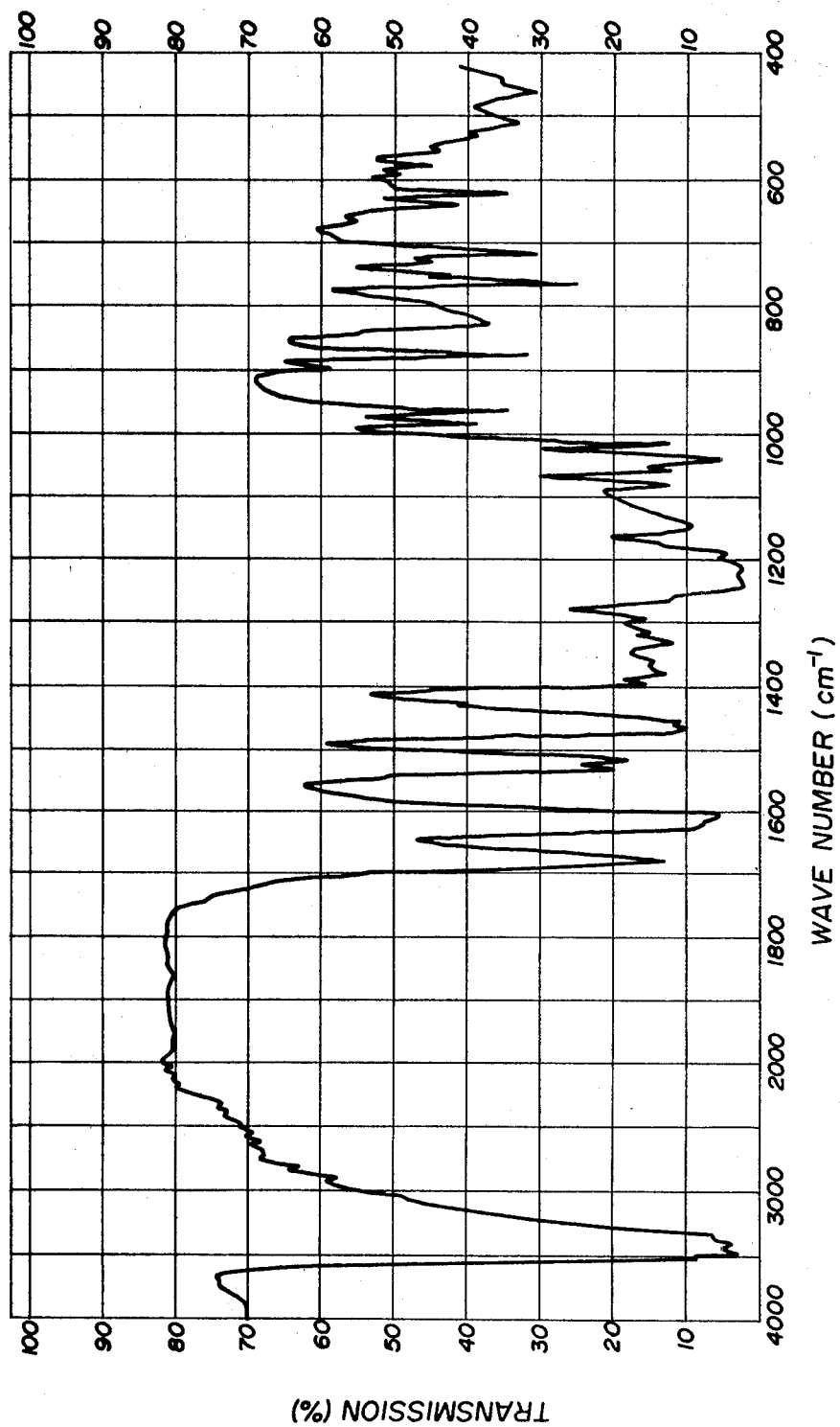
FIG. 5 is the infrared absorption spectrum of (—)epicatechin gallate.
Figure 6:
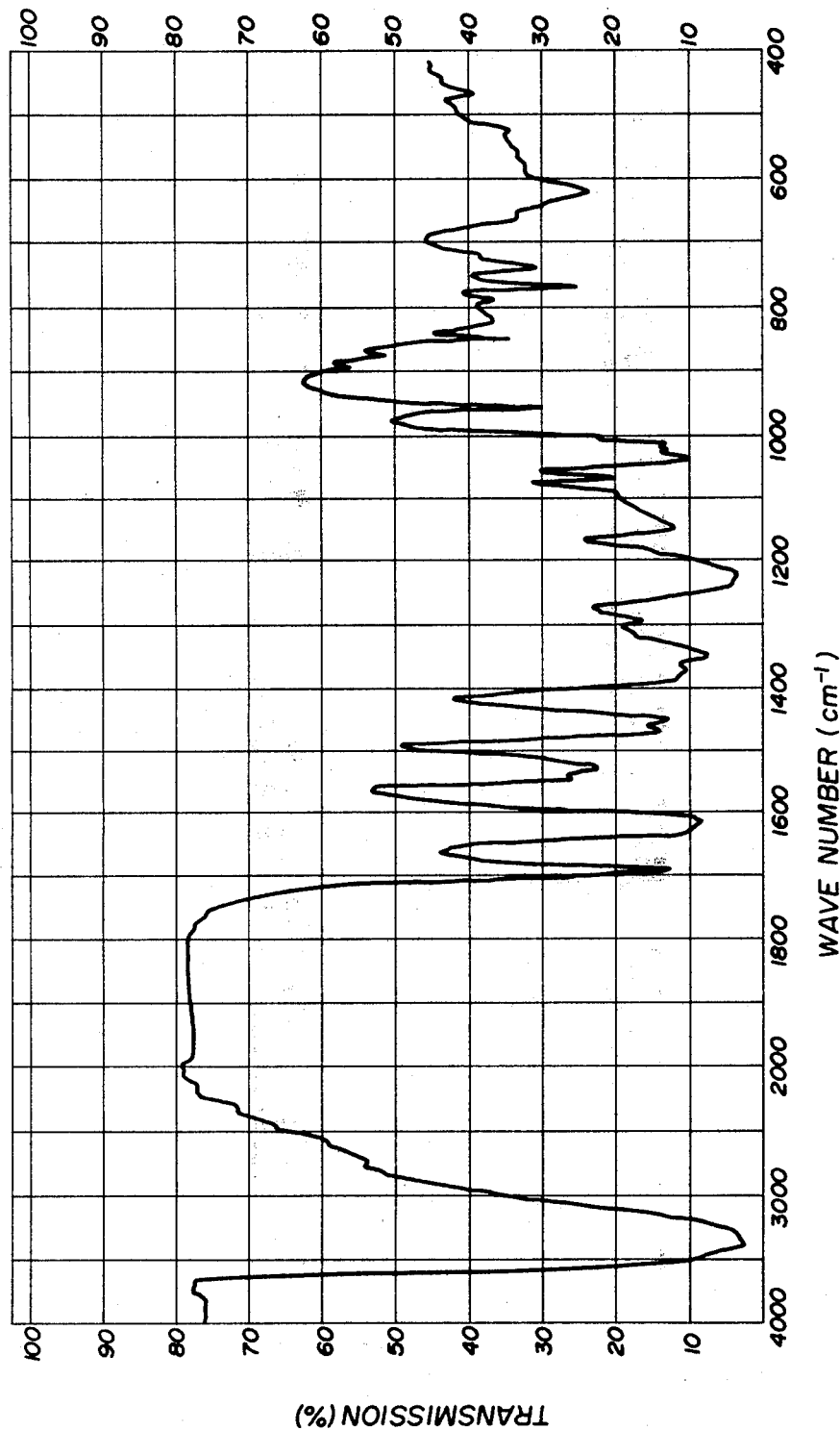
FIG. 6 is the infrared absorption spectrum of (—)epigallocatechin gallate.

The extraction of tannic substance from tea leaves can be carried out with water at an elevated temperature, preferably hot water or an organic solvent. Suitable organic solvents include, for example, acetone, alcohol and the like. They are preferably in an aqueous state. When the tannic substance is extracted with water at an elevated temperature, the extract is cooled and thereafter shaken with a solvent such as ethyl acetate, isobutyl methyl ketone, n-butylalcohol and the like, to which the tannic substance is allowed to transfer. After distilling out the solvent under reduced pressure, the residue is weighed and dissolved in water to form an aqueous solution. When the tannic substance is extracted with an organic solvent, the solvent is distilled out as described above and the tannic substance is weighed and dissolved in water.

Subsequently, an aqueous solution of caffeine is added to the aqueous solution of the tannic substance. At this time, caffeine should be added in a larger amount than the amount corresponding to the weight of tannin (i.e., the tannic substance) and desirably in a solution dissolved in an equivalent amount of water. After adding the aqueous solution of caffeine, the mixture is allowed to stand at low temperature of 0°–10° C., preferably about 3°–7° C., so as to separate the tannic substance, i.e. catechins, into two fractions containing the free catechins and the ester-type catechins respectively. When the caffeine is added, the solution of the tannic substance becomes turbid and begins to form a precipitate. After allowing the mixture to stand for 10–15 hours, it is separated into the supernatant (upper phase) and the precipitate (lower phase). The supernatant is mixed with a solution of caffeine in about one-half of the last added amount so as to form additional precipitate. Since the precipitate has high viscosity, it is added in an adequate amount of water (preferably an amount corresponding to the amount of water initially added) and is heated to dissolve it, and then mixed with a solution of caffeine in an amount about one-half of the first addition to form an additional precipitate as described for the supernatant. When the separation of the solid and the liquid is not thoroughly effected, the above procedure should be repeated. Each of the supernatants are combined and then shaken with an organic solvent. Ethyl acetate etc. is preferred as the organic solvent for this use. By this treatment, the free catechins contained in the supernatant transfer to the organic solvent together with caffeine, and, therefore, are separated from impurities. The solvent is then distilled off under reduced pressure to obtain the dry residue (consisting mainly of a mixture of the free catechins with caffeine).

After dissolving this dry residue in a small amount of water, caffeine is removed from the residue by shaking it several times with chloroform. The fractionation of the epicatechin component and the epigallocatechin component is carried out with a distribution solvent on a Sephadex column.

Each of the precipitates also are combined, dissolved in water and then shaken thoroughly with an organic solvent such as ethyl acetate and the like in a similar manner to that described for the supernatant to transfer the active components to the solvent and remove impurities such as brown substances and the like. The components transferred to the solvent consist substantially of a mixture of the ester-type catechins and caffeine. The organic solvent is thereafter distilled off under reduced pressure and the so-obtained dry residue is dissolved in water. Caffeine is completely removed by shaking the aqueous solution several times with chloroform. Epicatechin gallate and epigallocatechin gallate are fractionated with a distribution solvent on a Sephadex column.

Examples of columns used for the fractionation of the free catechins and the ester-type catechins include Sephadex LH20. The distribution column is filled with Sephadex using water. As the distribution solvent, a mixture of n-butyl alcohol, acetone and water is desirable, and an ideal proportion of the componets is 4:1:2. In this case, another solvent, which establishes the affinity of n-butyl alcohol with water, may be also employed instead of acetone. Methyl alcohol, ethyl alcohol, etc. are examples of such a solvent. Following the above distribution procedure, (−)epicatechin and (−)epigallocatechin are obtained from the supernatant; and (−)epicatechin gallate and (−)epigallocatechin gallate and gallic acid are obtained from the solution of the precipitate.

In order to obtain each component in crystalline form, it is dissolved in water after distilling out the distribution solvent under reduced pressure and then crystallized from water.

According to the present invention, each of four catechins is obtained simultaneously in a short time and by relatively simple procedures. Furthermore, toxic substances, which are harmful to human body, are not used for the production of catechins. The caffeine and the solvents can be recovered. Caffeine and gallic acid are obtained as by-products. The present invention provides a process having very high utility, which can produce catechins continuously and economically in a large yield corresponding to the raw materials. Therefore, the present invention contributes to the use of catechins in the chemical, biochemical, physiological and pharmaceutical field, and besides to the enlargement of the consumption and the steadiness of the production of tea.

Tea tannin is liable to be oxidized, even when it is sealed after drying. However, when each catechin is crystallized according to this invention, its oxidation proceeds very slowly and the properties of the catechin are hardly changed even in storage for a long period of time. I discovered that the four catechins of natural origin have a virucidal effect and can be combined with a mercury compound (HgCl etc.) to insolubilize it. It has been determined that (−)epicatechin gallate can be combined with cadmium even under strongly acidic conditions (pH 0.65). It has been also elucidated that infection with tobacco mosaic virus can be inhibited and components which can be combined to form various nucleic acids, can be obtained by treating one of these catechins with oxidase. In addition to this, it has been confirmed that among these chromatic components, theaflavine monogallate and digallate can be combined with cadmium. Free theaflavine most preferably can be combined with mercury compounds (HgCl etc.). The other theaflavines have similar characteristics.

Additionally, catechins and their oxides are studied as taste indicating substances, and, therefore, the application and the use of these components extend in various fields and will become wider in future.

The invention will now be more specifically described by the following Examples.

EXAMPLE

Ten cylindrical vessels are filled with 1 kilogram of tea leaves per vessel. Extraction is carried out in a semi-contercurrent continuous multi-stage apparatus in which hot water is poured into the first vessel and the extract is introduced into the second vessel. 120 milliliters of each initial effluent from the fifth to tenth vessel is taken and a total 720 milliliters of the combined effluent is cooled. After adding ethyl acetate to the aqueous solution, the solution is shaken so as to transfer the extracted tannic substances to the ethyl acetate layer. Ethyl acetate is distilled out at temperatures below 50° C. under reduced pressure to leave a residue. Thereafter 36 grams of the residue is dissolved in water. To the so obtained aqueous solution, an aqueous solution of caffeine is added in the same amount of the weight of the above residue and the mixture is maintained at a temperature of 5° C. After 15 hours, the mixture is separated into a supernatant (1) and a precipitate (1).

An aqueous solution of 18 grams of caffeine is added to the supernatant and allowed to stand at a temperature of from 5° C. to form a supernatant (2) and a precipitate (2) which are separated after 15 hours.

The precipitate (1) is dissolved in 500 milliliters of water by heating, mixed with an aqueous solution of 18 grams of caffeine and then allowed to stand at a temperature of 5° C. to form a supernatant (3) and a precipitate (3) which are separated after 15 hours.

The supernatant (2) is combined with the supernatant (3) and shaken thoroughly with ethyl acetate so as to transfer the components contained in the supernatant to the ethyl acetate layer and remove impurities.

Thereafter, the solvent is distilled off under reduced pressure and the residue is dissolved in water and shaken several times with chloroform to remove caffeine. The aqueous solution is poured into a column filled with Sephadex LH20 and subjected to fractionation by means of n-butyl alcohol/acetone/water (4:1:2) as the distribution solvent.

By this fractionation, the free catechins are fractionated into (−)epicatechin and (−)epigallocatechin. After the fractionation, the distribution solvent is distilled off and each residue is dissolved in water and crystallized from water to give 1.36 grams of (−)epicatechin and 1.87 grams of (−)epigallocatechin.

The precipitate (2) is combined with the precipitate (3) and dissolved in 500 milliliters of water. The so obtained aqueous solution is thoroughly shaken with ethyl acetate so as to transfer the components to the ethyl acetate layer and remove impurities.

The post-treatment is carried out in a similar manner to that of the supernatant to give 4.76 grams of (−)epicatechin gallate and 4.13 grams of (−)epigallocatechin gallate.

Sephadex LH20 is a trademark for a molecular sieve material.

The physical properties of the thus obtained catechins are reported in the following Tables and in the Drawings.

TABLE 1

Structure and properties of catechins

| Structural formula of catechins | Melting point of catechins | | |
|---|---|---|---|
| | Known sample (A) °C. | Known sample (B) °C. | Sample of this invention °C. |
| (−) epicatechin $C_{15}H_{14}O_6$ | 236–237 | 230 | 231 |
| (−) epigallocatechin $C_{15}H_{14}O_7$ | 217–218 | 210 | 217 |
| (−) epicatechin gallate $C_{22}H_{18}O_{10}$ | 252–254 | 230 | 238 |
| (−) epigallocatechin gallate $C_{22}H_{18}O_{11}$ | 215–216 | 220 | 220–221 |

TABLE 2

Found and calculated data of mixed crystals of catechin and caffeine

| Mixed crystal | m.p. °C. | Elementary analysis | | | | | | Note |
|---|---|---|---|---|---|---|---|---|
| | | Found | | | Calculated | | | |
| | | C | H | N | C | H | N | |
| (−) Epicatechin : Caffeine | 150 | 52.72 | 5.54 | 10.55 | 57.02 | 4.99 | 11.56 | 1:1 (mixing ratio) |
| | | | | | 54.87 | 5.01 | 16.52 | 1:2 " |
| (−)Epigallo- catechin : Caffeine | 186 | 54.84 | 5.01 | 11.13 | 55.20 | 4.83 | 11.20 | 1:1 " |
| | | | | | 53.60 | 4.90 | 16.14 | 1:2 " |
| (−) Epicatechin gallate : Caffeine | 160 | 51.75 | 5.15 | 13.18 | 56.60 | 4.40 | 8.81 | 1:1 " |
| | | | | | 54.93 | 4.58 | 13.49 | 1:2 " |
| (−) Epigallo- catechin gallate : Caffeine | — | 49.50 | 5.28 | 28.42 | 53.50 | 4.49 | 13.24 | 1:2 " |
| | | | | | 49.60 | 5.14 | 28.45 | 1:160 " |

REFERENCE EXAMPLE

The inhibiting effect of infection with tobacco mosaic virus is determined on the product which is obtained by treating (−)epigallocatechin gallate obtained in the Example with oxidase. The test is carried out by administering to the tobacco By-4, 142 ppm of the product treated with oxidase by the hydroponic method, inoculating the whole surface of the lower sound third leaf with tobacco mosaic virus (inoculating source) and evaluating the infection of young leaves. The evaluation is carried out by cutting and treating the young leaves and comparing with the half-leaf inoculation of N. glutinosa. In the control zone, only water is given to the plants. The results are summarized in Table 3.

TABLE 3

| Days after inoculation | Number of tests | Number of pathognomonic markings | |
|---|---|---|---|
| | | in the control zone (non-treated/inocu- lating source) | in the treated zone (treated/ inoculating source) |
| 7 | 1 | 4/495 | 0/689 |
| | 2 | 4/464 | 0/550 |
| | 3 | 23/686 | 0/520 |
| 11 | 1 | 1213/412 | 0/591 |
| | 2 | 1250/490 | 0/522 |
| | 3 | 922/464 | 0/432 |

I claim:

1. A process for producing catechins comprising admixing an aqueous caffeine solution with an aqueous solution of tannic substance which has been extracted from tea leaves to form free catechin compounds selected from the group consisting of epicatechin and epigallocatechin and esters of catechin compounds selected from the group consisting of epicatechin gallate and epigallocatechin gallate.

2. The process of claim 1 wherein the aqueous solution of tannic substance is prepared by contacting tea leaves with water at an elevated temperature, or with an organic solvent to extract the tannic substance from the tea leaves, and then forming an aqeuous solution of said tannic substance.

3. The process of claim 1 wherein said aqueous solution of caffeine contains an amount of caffeine by weight which is larger than the amount of tannin by weight in said aqueous solution of tannic substance.

4. The process of claim 1 for producing catechins comprising admixing an aqueous solution of caffeine with an aqueous solution of tannic substance which has been extracted from tea leaves by contacting the tea leaves with water at an elevated temperature, or by contacting the tea leaves with an organic solvent, to form a precipitate of epicatechin gallate and epigallocatechin gallate and a supernatant liquid containing epicatechin and epigallocatechin, separating said precipitate from said supernatant liquid,
  removing caffeine from the admixture of epicatechin and epigallocatechin, and separately from the admixture of epicatechin gallate and epigallocatechin gallate, and then fractionating the mixture of epicatechin and epigallocatechin and separately fractionating the mixture of epicatechin gallate and epigallocatechin gallate to obtain the respective compounds.

5. The process of claim 4 wherein the admixture of the aqueous solution of caffeine and the aqueous solution of tannic substance is at a temperature of between 0° and 10° C. until said precipitate forms.

6. The process of claim 4 or claim 5 wherein said aqueous solution of caffeine contains an amount of caffeine by weight which is larger than the amount of tannin by weight in said aqueous solution of tannic substance.

7. The process of claim 4 or claim 5 wherein the respective mixture of (1) epicatechin and epigallocatechin, and (2) epicatechin gallate and epigallocatechin gallate, are fractionated with the distribution solvent on a column comprising a molecular sieve material.

8. The process of claim 4 wherein caffeine is removed by contacting the caffeine containing materials with chloroform which preferentially dissolves the caffeine.

9. The process of claim 6 wherein the respective mixture of (1) epicatechin and epigallocatechin, and (2) epicatechin gallate and epigallocatechin gallate, are fractionated with the distribution solvent on a column comprising a molecular sieve material.

* * * * *